US012758698B2

(12) United States Patent
Nazerali et al.

(10) Patent No.: US 12,758,698 B2
(45) Date of Patent: Oct. 13, 2026

(54) BREAST POCKET IRRIGATION APPARATUSES AND METHODS

(71) Applicant: TELA Bio, Inc., Malvern, PA (US)

(72) Inventors: Rahim Nazerali, Menlo Park, CA (US); Raymond Buzz Bonneau, San Francisco, CA (US)

(73) Assignee: TELA Bio, Inc., Malvern, PA (US)

( * ) Notice: Subject to any disclaimer, the term of this patent is extended or adjusted under 35 U.S.C. 154(b) by 650 days.

(21) Appl. No.: 18/307,709

(22) Filed: Apr. 26, 2023

(65) Prior Publication Data

US 2023/0338637 A1 Oct. 26, 2023

Related U.S. Application Data

(60) Provisional application No. 63/335,009, filed on Apr. 26, 2022.

(51) Int. Cl.
*A61M 1/00* (2006.01)

(52) U.S. Cl.
CPC .................................... *A61M 1/77* (2021.05)

(58) Field of Classification Search
CPC ........ A61M 1/77; A61M 1/85; A61M 3/0279; A61M 3/0283; A61F 4/15; A61F 13/05
See application file for complete search history.

(56) References Cited

U.S. PATENT DOCUMENTS

| | | | |
|---|---|---|---|
| 2,259,025 | A | 10/1941 | Cosgro |
| 3,033,139 | A | 5/1962 | Tateishi |
| 3,054,406 | A | 9/1962 | Usher |
| 3,155,095 | A | 11/1964 | Brown |
| 3,364,200 | A | 1/1968 | Ashton et al. |
| 3,658,023 | A | 4/1972 | Rossi |
| 4,466,370 | A | 8/1984 | Eguchi et al. |
| 5,593,441 | A | 1/1997 | Lichtenstein et al. |
| 5,634,931 | A | 6/1997 | Kugel |
| 5,683,400 | A | 11/1997 | McGuire |
| 5,707,395 | A | 1/1998 | Li |
| 5,723,010 | A | 3/1998 | Yui et al. |
| 5,919,232 | A | 7/1999 | Chaffringeon et al. |
| 5,990,378 | A | 11/1999 | Ellis |
| 6,120,539 | A | 9/2000 | Eldridge et al. |
| 6,258,124 | B1 | 7/2001 | Darois et al. |

(Continued)

FOREIGN PATENT DOCUMENTS

| | | |
|---|---|---|
| CN | 113693821 A | 11/2021 |
| CN | 217593430 U | 10/2022 |

(Continued)

OTHER PUBLICATIONS

KR 20070122546 A machine translation (Year: 2007).*

(Continued)

*Primary Examiner* — Laura A Bouchelle
(74) *Attorney, Agent, or Firm* — Shay Glenn LLP

(57) ABSTRACT

A subcutaneous irrigation apparatus comprising a flexible base comprising one or more size adjustment channels and a plurality of irrigation lumens and a hub coupled to the flexible base. The hub may include an inlet port, an outlet port, and a suction port, wherein the plurality of irrigation lumens extend from the hub. These apparatuses may be configured to apply irrigation as a vortex within the body.

20 Claims, 7 Drawing Sheets

(56) References Cited

U.S. PATENT DOCUMENTS

| | | | |
|---|---|---|---|
| 6,319,264 | B1 | 11/2001 | Törmälä et al. |
| 6,371,985 | B1 | 4/2002 | Goldberg |
| 6,383,201 | B1 | 5/2002 | Dong |
| 6,652,595 | B1 | 11/2003 | Nicolo |
| 6,814,748 | B1 | 11/2004 | Baker et al. |
| 6,962,120 | B1 | 11/2005 | Fujikura et al. |
| 7,824,420 | B2 | 11/2010 | Eldridge et al. |
| 7,883,494 | B2 * | 2/2011 | Martin .................. A61M 3/022 604/289 |
| 7,946,236 | B2 | 5/2011 | Butcher |
| 8,074,591 | B2 | 12/2011 | Butcher et al. |
| 8,182,545 | B2 | 5/2012 | Cherok et al. |
| 8,236,342 | B2 | 8/2012 | Thomas et al. |
| 8,853,294 | B2 | 10/2014 | Myung et al. |
| 8,974,428 | B2 * | 3/2015 | Freedman ........... A61M 3/0279 604/304 |
| 9,205,052 | B2 | 12/2015 | Kim et al. |
| 9,289,279 | B2 | 3/2016 | Wilson et al. |
| 9,295,757 | B2 | 3/2016 | Patel et al. |
| 9,326,840 | B2 | 5/2016 | Mortarino |
| 9,364,310 | B2 | 6/2016 | Stopek |
| 9,421,079 | B2 | 8/2016 | Koullick et al. |
| 9,468,705 | B2 | 10/2016 | Geller |
| 9,510,925 | B2 | 12/2016 | Hotter et al. |
| 9,554,887 | B2 | 1/2017 | Lecuivre |
| 9,585,838 | B2 | 3/2017 | Hartounian et al. |
| 9,770,414 | B2 | 9/2017 | Garcia et al. |
| 9,775,700 | B2 | 10/2017 | Greenhalgh et al. |
| 9,820,843 | B2 | 11/2017 | Greenhalgh et al. |
| 9,925,030 | B2 | 3/2018 | Greenhalgh et al. |
| 10,130,457 | B2 | 11/2018 | Greenhalgh et al. |
| 10,213,284 | B2 | 2/2019 | Greenhalgh et al. |
| 10,426,587 | B2 | 10/2019 | Greenhalgh et al. |
| 10,500,030 | B2 | 12/2019 | Greenhalgh et al. |
| 10,561,485 | B2 | 2/2020 | Greenhalgh et al. |
| 10,675,141 | B2 | 6/2020 | Greenhalgh et al. |
| 10,702,364 | B2 | 7/2020 | Greenhalgh et al. |
| 11,344,397 | B2 | 5/2022 | Greenhalgh et al. |
| 11,369,464 | B2 | 6/2022 | Greenhalgh et al. |
| 11,426,156 | B2 | 8/2022 | Coleman et al. |
| 11,446,130 | B2 | 9/2022 | Greenhalgh et al. |
| 11,464,616 | B2 | 10/2022 | Greenhalgh et al. |
| 11,590,262 | B2 | 2/2023 | Greenhalgh |
| 11,628,054 | B2 | 4/2023 | Greenhalgh et al. |
| 2001/0020188 | A1 | 9/2001 | Sander |
| 2002/0111392 | A1 | 8/2002 | Cruise |
| 2003/0023316 | A1 | 1/2003 | Brown et al. |
| 2003/0225355 | A1 | 12/2003 | Butler |
| 2004/0010320 | A1 | 1/2004 | Huckle et al. |
| 2004/0033212 | A1 | 2/2004 | Thomson et al. |
| 2004/0054376 | A1 | 3/2004 | Ory et al. |
| 2004/0078089 | A1 | 4/2004 | Ellis et al. |
| 2004/0138762 | A1 | 7/2004 | Therin et al. |
| 2004/0249457 | A1 | 12/2004 | Smith et al. |
| 2005/0070930 | A1 | 3/2005 | Kammerer |
| 2005/0113849 | A1 | 5/2005 | Popadiuk et al. |
| 2005/0113938 | A1 | 5/2005 | Jamiolkowski et al. |
| 2005/0118236 | A1 | 6/2005 | Qiu et al. |
| 2005/0255543 | A1 | 11/2005 | Just et al. |
| 2006/0178683 | A1 | 8/2006 | Shimoji et al. |
| 2006/0217747 | A1 | 9/2006 | Ferree |
| 2006/0229722 | A1 | 10/2006 | Bianchi et al. |
| 2007/0088434 | A1 | 4/2007 | Frank |
| 2007/0190108 | A1 | 8/2007 | Datta et al. |
| 2007/0224238 | A1 | 9/2007 | Mansmann et al. |
| 2007/0250147 | A1 | 10/2007 | Walther et al. |
| 2008/0097601 | A1 | 4/2008 | Codori-Hurff et al. |
| 2008/0167729 | A1 | 7/2008 | Nelson et al. |
| 2008/0181928 | A1 | 7/2008 | Hakimi-Mehr et al. |
| 2009/0018655 | A1 | 1/2009 | Brunelle et al. |
| 2009/0054339 | A1 | 2/2009 | Marshall et al. |
| 2009/0069893 | A1 | 3/2009 | Paukshto et al. |
| 2009/0082864 | A1 | 3/2009 | Chen et al. |
| 2009/0149939 | A1 | 6/2009 | Godlewski et al. |
| 2009/0216338 | A1 | 8/2009 | Gingras et al. |
| 2009/0306688 | A1 | 12/2009 | Patel et al. |
| 2009/0326577 | A1 | 12/2009 | Johnson et al. |
| 2010/0010114 | A1 | 1/2010 | Myung et al. |
| 2010/0028396 | A1 | 2/2010 | Ward et al. |
| 2010/0063599 | A1 | 3/2010 | Brunelle et al. |
| 2010/0100107 | A1 | 4/2010 | Duggal et al. |
| 2010/0120679 | A1 | 5/2010 | Xu et al. |
| 2010/0217388 | A1 | 8/2010 | Cohen et al. |
| 2010/0249929 | A1 | 9/2010 | Kurz et al. |
| 2010/0254900 | A1 | 10/2010 | Campbell et al. |
| 2010/0305500 | A1 | 12/2010 | Lambert et al. |
| 2010/0311949 | A1 | 12/2010 | Akkus et al. |
| 2010/0318108 | A1 | 12/2010 | Datta et al. |
| 2010/0318124 | A1 | 12/2010 | Leung et al. |
| 2011/0014153 | A1 | 1/2011 | Derwin et al. |
| 2011/0020420 | A1 | 1/2011 | Bosley et al. |
| 2011/0125287 | A1 | 5/2011 | Hotter et al. |
| 2011/0196490 | A1 | 8/2011 | Gadikota et al. |
| 2011/0250264 | A1 | 10/2011 | Schutt et al. |
| 2011/0257761 | A1 | 10/2011 | Mortarino |
| 2011/0301717 | A1 | 12/2011 | Becker |
| 2012/0010637 | A1 | 1/2012 | Stopek et al. |
| 2012/0035608 | A1 | 2/2012 | Marchitto et al. |
| 2012/0082712 | A1 | 4/2012 | Stopek et al. |
| 2012/0095482 | A1 | 4/2012 | Peterson et al. |
| 2012/0143329 | A1 | 6/2012 | Kim |
| 2012/0165957 | A1 | 6/2012 | Everland et al. |
| 2012/0179176 | A1 | 7/2012 | Wilson et al. |
| 2012/0184974 | A1 | 7/2012 | Becker |
| 2012/0253464 | A1 | 10/2012 | Hwang et al. |
| 2013/0064772 | A1 | 3/2013 | Swiss et al. |
| 2013/0116799 | A1 | 5/2013 | Derwin et al. |
| 2013/0172994 | A1 | 7/2013 | Becker |
| 2013/0197300 | A1 | 8/2013 | Koullick et al. |
| 2013/0209547 | A1 | 8/2013 | Garcia et al. |
| 2013/0211307 | A1 | 8/2013 | Evans et al. |
| 2013/0267137 | A1 | 10/2013 | Peniston et al. |
| 2013/0303958 | A1 | 11/2013 | Holm et al. |
| 2013/0304098 | A1 | 11/2013 | Mortarino |
| 2013/0317286 | A1 | 11/2013 | Bluecher et al. |
| 2014/0090942 | A1 | 4/2014 | Schlipper |
| 2014/0094931 | A1 | 4/2014 | Derwin et al. |
| 2014/0182498 | A1 | 7/2014 | Torigoe |
| 2014/0276993 | A1 | 9/2014 | Reilly et al. |
| 2014/0364878 | A1 | 12/2014 | Ladet et al. |
| 2015/0112434 | A1 | 4/2015 | Felix et al. |
| 2015/0127103 | A1 | 5/2015 | Seedhom |
| 2015/0267330 | A1 | 9/2015 | Carrier et al. |
| 2015/0297798 | A1 | 10/2015 | Badylak et al. |
| 2016/0058534 | A1 | 3/2016 | Derwin et al. |
| 2016/0058589 | A1 | 3/2016 | Bar et al. |
| 2016/0136289 | A1 | 5/2016 | Puri et al. |
| 2016/0206580 | A1 | 7/2016 | Los et al. |
| 2016/0262208 | A1 | 9/2016 | Hsieh |
| 2016/0374791 | A1 | 12/2016 | Lecuivre et al. |
| 2017/0027679 | A1 | 2/2017 | Serban et al. |
| 2017/0086972 | A1 | 3/2017 | Braido et al. |
| 2017/0245847 | A1 | 8/2017 | Obermiller et al. |
| 2018/0098836 | A1 | 4/2018 | Lee et al. |
| 2019/0008623 | A1 | 1/2019 | Nemoto et al. |
| 2019/0234937 | A1 | 8/2019 | Wang et al. |
| 2020/0238604 | A1 | 7/2020 | Hart et al. |
| 2020/0297476 | A1 | 9/2020 | Greenhalgh et al. |
| 2020/0360129 | A1 | 11/2020 | Moses et al. |
| 2021/0030925 | A1 | 2/2021 | Lopez et al. |
| 2021/0093444 | A1 | 4/2021 | Feinberg et al. |
| 2021/0128793 | A1 | 5/2021 | Mongrain et al. |
| 2021/0212863 | A1 | 7/2021 | Xia et al. |
| 2021/0290416 | A1 | 9/2021 | Hall et al. |
| 2021/0315690 | A1 | 10/2021 | Morin et al. |
| 2021/0322666 | A1 | 10/2021 | Greener |
| 2021/0338405 | A1 | 11/2021 | Bluecher et al. |
| 2022/0105238 | A1 | 4/2022 | Reimer et al. |
| 2022/0110749 | A1 | 4/2022 | Hariton et al. |
| 2022/0118416 | A1 | 4/2022 | Pathak et al. |
| 2022/0126013 | A1 | 4/2022 | Selby et al. |
| 2022/0133465 | A1 | 5/2022 | Rocco et al. |
| 2022/0211367 | A1 | 7/2022 | Schmid et al. |
| 2022/0273412 | A1 | 9/2022 | Greenhalgh et al. |

(56) References Cited

U.S. PATENT DOCUMENTS

| | | | |
|---|---|---|---|
| 2022/0296350 | A1 | 9/2022 | Greenhalgh et al. |
| 2023/0008637 | A1 | 1/2023 | Greenhalgh et al. |
| 2023/0293281 | A1 | 9/2023 | Greenhalgh et al. |
| 2025/0041040 | A1 | 2/2025 | Greenhalgh et al. |
| 2025/0049552 | A1 | 2/2025 | Greenhalgh et al. |
| 2025/0090295 | A1 | 3/2025 | Greenhalgh et al. |
| 2025/0268701 | A1 | 8/2025 | Greenhalgh et al. |
| 2025/0387543 | A1 | 12/2025 | Greenhalgh |

FOREIGN PATENT DOCUMENTS

| | | | | | |
|---|---|---|---|---|---|
| DE | 10312674 | A1 | | 10/2003 | |
| DE | 112007001732 | T5 | | 4/2011 | |
| EP | 2198854 | A2 | | 6/2010 | |
| EP | 2229918 | A1 | | 9/2010 | |
| EP | 2300066 | A2 | | 3/2011 | |
| EP | 2344133 | A2 | | 7/2011 | |
| JP | 2015025033 | A | | 2/2015 | |
| KR | 20070122546 | A | * | 12/2007 | ............ A61M 35/30 |
| RU | 2524196 | C2 | | 7/2014 | |
| WO | WO00/57812 | A1 | | 10/2000 | |
| WO | WO02/078568 | A1 | | 10/2002 | |
| WO | WO03/082363 | A1 | | 10/2003 | |
| WO | WO03/094781 | A1 | | 11/2003 | |
| WO | WO2008/095038 | A1 | | 8/2008 | |
| WO | WO2012/017415 | A2 | | 2/2012 | |
| WO | WO-2012138514 | A1 | * | 10/2012 | ............ A61M 27/00 |
| WO | WO2017/050837 | A1 | | 3/2017 | |
| WO | WO2017/191276 | A1 | | 11/2017 | |
| WO | WO2017/223462 | A1 | | 12/2017 | |

OTHER PUBLICATIONS

Greenhalgh et al.; U.S. Appl. No. 18/511,680 entitled "Corner-lock stitch patterns," filed Nov. 16, 2023.

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.

Franklin et al.; Uptake of tetracycline by aortic aneurysm wall and its effect on inflammation and proteolysis; British Journal of Surgery; 86(6); pp. 771-775; Jun. 1999.

Mayo Clinic;Placement of Breast Implants; retrieved May 25, 2017 from http://www.mayoclinic.org/placement-of-breast-implants/img-20007384; 1 pg; May 25, 2017.

Pyo et al.; Targeted gene disruption of matrix metalloproteinase-9 (gelatinase B) suppresses development of experimental abdominal aortic aneurysms; The journal of Clinical Investigation; 105(11); pp. 1641-1649; Jun. 2000.

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdominal aortic; Circulation; 100; pp. 48-54, 8 pages; Jul. 1999.

Xu et al.; Sp1 increases expression of cyclooxygenase-2 in hypoxic vascular endothelium implications for the mechanisms of aortic aneurysm and heart failure; journal of Biological Chemistry; 275(32); pp. 24583-24589; Aug. 2000.

Greenhalgh et al.; U.S. Appl. No. 17/938,250 entitled "Hernia repair grafts having anti-adhesion barriers," filed Oct. 5, 2022.

Greenhalgh ; U.S. Appl. No. 18/157,653 entitled "Surgical repair graft," filed Jan. 20, 2023.

Nazerali; U.S. Appl. No. 17/447,166 entitled "Subcutaneous and pocket irrigator," filed Sep. 8, 2021.

Greenhalgh et al.; U.S. Appl. No. 18/664,253 entitled "Surgical repair graft," filed May 14, 2024.

Greenhalgh et al.; U.S. Appl. No. 19/009,833 entitled "Textured medical textiles," filed Jan. 3, 2025.

Romano et al.; U.S. Appl. No. 18/353,858 entitled "Nonuniform embroidered soft tissue implant structure," filed Jul. 17, 2023.

* cited by examiner

BREAST POCKET IRRIGATION APPARATUSES AND METHODS

CLAIM OF PRIORITY

This patent application claims priority to U.S. Provisional Patent Application No. 63/335,009, titled "BREAST POCKET IRRIGATION SYSTEM" filed on Apr. 26, 2022, which is hereby incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Irrigation is used to remove debris and prevent infection during surgical outcomes. Breast augmentation is an example of a surgical procedure involving the formation of a subcutaneous pocket or space where an implant can be inserted. The pocket can be susceptible to increased bacterial activity and formation of biofilm resulting in capsular contracture, a condition whereby tissue around the implant thickens and tightens resulting in a distorted appearance that may require corrective intervention. Accordingly, irrigating a breast pocket can reduce the potential for capsular contracture and improve surgical outcomes.

Current irrigation techniques and mechanisms often rely on hand-operated wand or elongate tools to introduce antimicrobial or antiseptic irrigation fluids into a breast pocket. These tools fail to provide consistent and effective irrigation of a breast pocket and often introduce additional error associated with a lack of irrigation coverage.

For these reasons, it would be desirable to provide improved methods, systems, and tools for subcutaneous irrigation. It would be particularly desirable to provide simplified deployment systems with adjustable sizes, even more desirably, to provide consistent irrigation with flow rates and patterns to promote improved surgical outcomes. At least some of these objectives will be met by the various embodiments that follow.

SUMMARY OF THE DISCLOSURE

In general, the subcutaneous irrigation apparatuses (e.g., devices, systems, etc.) described herein may include a flexible base comprising one or more size adjustment channels and a plurality of irrigation lumens and a hub coupled to the flexible base. The hub can comprise an inlet port, an outlet port, and a suction port, wherein the plurality of irrigation lumens extend from the hub. The hub may be central or offset.

In this and other examples, a subcutaneous irrigation apparatus can also include one or more of the following: one or more holes extending into each irrigation lumen through the flexible base. The hub can be integrated with the flexible base. The hub can be configured to distribute fluid through the plurality of irrigation lumens. The flexible base can comprise a perimeter configured to be reduced by the one or more size adjustment channels. Each of the plurality of irrigation lumens can be positioned at an angle between the hub and perimeter of the flexible base. The plurality of irrigation lumens can be configured to direct a vortex flow of irrigation fluid. The flexible base may comprise the hub. The plurality of irrigation lumens may extend radially from the hub. The subcutaneous irrigation apparatus may further comprise a flow control valve configured to adjust a flow rate of irrigation fluid. The flexible base can be configured to be inserted into a breast pocket.

In general, a breast pocket irrigation apparatus can include a flexible base with one or more size adjustment channels configured to reduce a perimeter of the flexible base, one or more irrigation tubes coupled to the flexible base, and a hub comprising an inlet port, outlet port, and suction port, wherein a proximal end of each irrigation tube is in communication with the hub. The hub may be a central hub.

In this and other examples, a breast pocket irrigation apparatus can also comprise one or more of the following: The one or more irrigation tubes can be angularly positioned around the flexible base and configure to provide a vortex flow of irrigation fluid into the breast pocket. Each irrigation tube can comprise one or more holes extending into a lumen of the irrigation tube. The inlet port can be configured to couple with an irrigation fluid source. The hub can be configured to distribute an irrigation fluid from the inlet port to each of the irrigation tubes.

In general, a method of irrigating a breast pocket can comprise adjusting a size of a breast pocket irrigation apparatus having a flexible base with size adjustment channels, then inserting the flexible base into the breast pocket, then initiating a flow of irrigation fluid through a hub of the breast pocket irrigation apparatus, wherein the hub distributes the irrigation fluid through irrigation tubes coupled to the flexible base.

In some examples, a method of irrigating a breast pocket can also comprise removing the irrigation fluid from within the breast pocket via a suction port coupled to the hub. The flow of irrigation fluid can be distributed by the irrigation tubes in a vortex pattern. Adjusting the size of the breast pocket irrigation apparatus comprises removing one or more segments of the flexible base via the size adjustment channels.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

Subcutaneous irrigation apparatuses (e.g., systems, devices, etc.), components thereof, and methods of use are described herein. These apparatuses may be configured to generate a vortex within the tissue into which they are inserted. By forming a vortex, the apparatus may more effectively wash and remove material from the region of tissue being treated, improving outcomes.

For example, a subcutaneous irrigation apparatus can include a flexible base with one or more irrigation tubes each extending outward at a vortex angle that is configured to result in a vortex, and a hub in communication with the irrigation tubes. The hub may be centrally positioned relative to the flexible base and can have an inlet tube (e.g., inlet port) and outlet tube (e.g., outlet port) configured to engage a fluid source and an irrigation removal (e.g. suction) source operably coupled with the outlet tube. The irrigation tubes can be integrated with the flexible base and are generally configured to direct a flow of irrigation fluid from the fluid source within a surgical site for irrigation, and in particular for forming a vortex in some modes of operation. Each of the fluid tubes can have a lumen extending therethrough from a distal end of the irrigation to the hub.

Figure 1A:
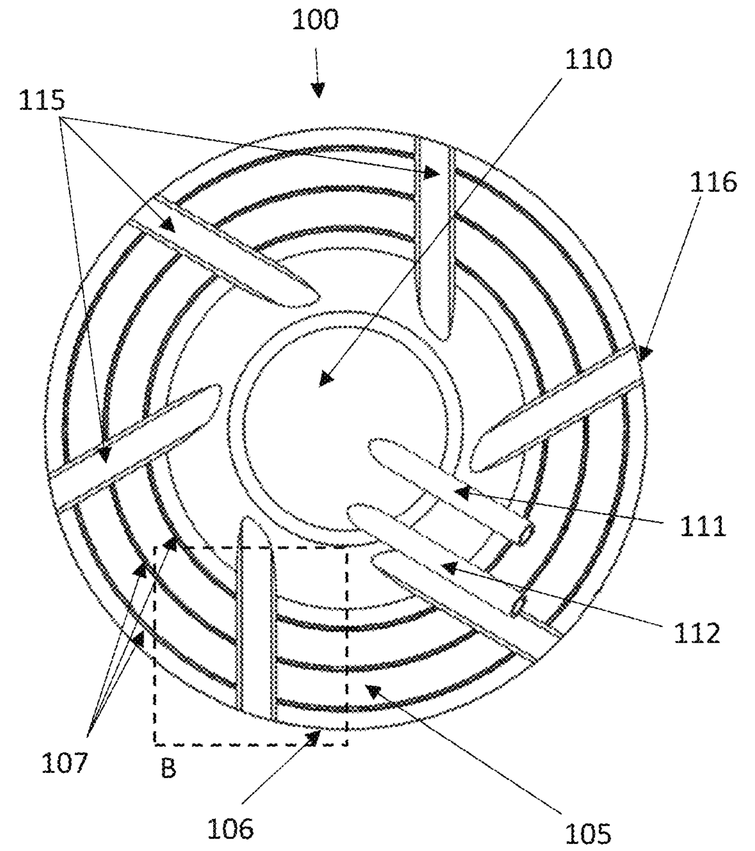
FIG. 1A shows a top view illustration of a subcutaneous irrigation apparatus as described herein.

FIG. 1A shows an example of a subcutaneous irrigation apparatus 100 from a top view. The flexible base 105 has a generally circular shape (which may be substantially flat) with the hub 110 positioned near a center of the flexible base 105 in this embodiment. Several channels (e.g., irrigation tubes) 115 are shown extending outward from a center of the flexible base 105. Hub 110 is shown with an inlet tube 111 and outlet tube 112 that can be configured to couple with a fluid source (not shown) and/or source of negative pressure. From this view, an outer perimeter 106 of the flexible base 105 is shown having a generally circular geometry. In some examples, the flexible base 105 is configured to have selectively adjustable dimensions such as a diameter of the perimeter 106. For example, any of these apparatuses may be configured to controllably and easily adjust size, e.g., by removing material from the base and/or channels.

For example, FIG. 1A illustrates size adjustment features 107 positioned at a distance proximal to a center of the flexible base, relative to the perimeter 106. In this example, the adjustment features 107 are generally concentric circular features each with a decreased diameter as they are positioned proximal to the center of the flexible base 105. These size adjustment features may be removal channels, which may be configured as frangible regions, perforations, slits, slots, tear-away regions, etc. that are configured to controllably and predictably control the removal of a predetermined amount, shape and location of material from the apparatus. For example, in FIG. 1A the size adjustment features 107 are configured as concentric channels (forming rings) that may be removed from the device, reducing the diameter of the device, in a predictable manner. These removal channels may have a thickness that is significantly thinner than the adjacent regions and may extend over and/or through the tubes 115 ("irrigation tubes"). In some examples removing material from the flexible base using the removal channel may also remove a corresponding region of the channels, e.g., the portion of the channels overlapping with the base region being removed. In some examples removing regions of the base using the removal channels may result in leaving behind all or a part of the channels.

Irrigation tubes 115 can have a lumen extending from a distal end 116 to the hub 110 and are configured to direct a flow of irrigation fluid from the fluid source out of the irrigation apparatus 100 to irrigate the surgical site (e.g., a breast pocket). Although FIG. 1A illustrates an example of a subcutaneous irrigation system 100 having six irrigation tubes 115, a subcutaneous irrigation apparatus may comprise any number of irrigation tubes. For example, a subcutaneous irrigation system may comprise one or more (two or more, three or more, four or more, five or more, etc.) irrigation tubes in operable communication with the flexible base and hub. Preferably, in order to generate a vortex the apparatus may include three or more (four or more, fiver or more, six or more, etc.) irrigation tubes.

Figure 1B:
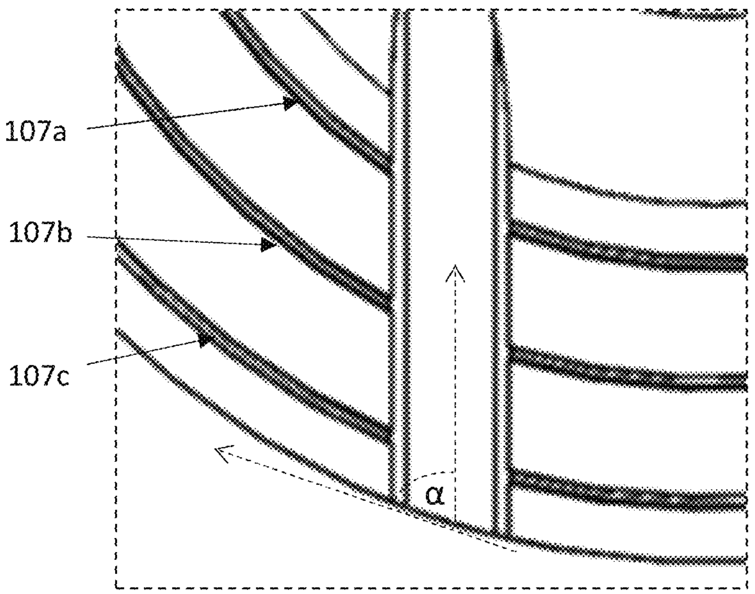
FIG. 1B shows a detailed view of size adjustment features of a subcutaneous irrigations apparatus as illustrated in FIG. 1A.

The irrigation tubes 115 may be arranged on the flexible base in a manner to provide (e.g., direct) a flow pattern of the irrigation fluid around the subcutaneous irrigation system. In particular, the configuration of the irrigation tubes may be configured to result in a vortex flow around the tissue, e.g., breast pocket. For example, FIG. 1A illustrates six irrigation tubes 115 extending from a perimeter of the hub 110 in an angular arrangement of the irrigation tubes can be configured to provide a flow of irrigation fluid in a flow pattern around the irrigation system. Considering an irrigation fluid flowing from the irrigation tubes 115 in FIG. 1A, the positioning of the irrigation tubes can provide a vortex fluid flow pattern that can be configured to swirl the fluid within a surgical site such as a breast pocket. In some examples, the flow pattern may be configured to improve irrigation. In some examples, the irrigation tubes 115 may be arranged in an angular manner relative to the long axis of the lumen and the edge of the flexible base 105 as illustrated by FIG. 1B. In some examples, the irrigation tubes may be arranged in a straight manner extending outward from the center of the flexible base 105. In some examples, irrigation tubes may be generally linear. In some examples, irrigation tubes may be curved from a distal end to a proximal end adjacent to or coupled with the hub 110.

As shown in FIG. 1B the angle (a) between the irrigation lumen and the edge or rim of the flexible base may be configured to be within a vortex angle that may result in a vortex when operating within applied fluid flow and/or pressures. For example, the vortex angle may correspond to an angle of between about 10 degrees and about 80 degrees between a midline down the length of the irrigation lumen and a line tangent to a rim of the flexible base from a point where the midline intersects the rim of the flexible base. In some examples the vortex angle (a) is between about 20 degrees and about 75 degrees. The flow rate may be relatively low (e.g., greater than 10 mL/hour, greater than 15 mL/hour, greater than 20 mL/hour, greater than 30 mL/hour, greater than 40 mL/hour, greater than 50 mL/hour, greater than 100 mL/hour, greater than 150 ml/hour, greater than 200 mL/hour, greater than 250 mL/day, etc.). In some examples the flow rate may be greater than 1 mL/min, greater than 5 mL/min, greater than 10 mL/min, greater than 20 mL/min, greater than 30 mL/min, etc., greater than 40 mL/min, etc.).

The flow rate may be varied. For example, period of high flow (vortex flow) may be alternated with periods of relatively low flow. In some examples high flow may result in a vortex, while low flow may result in saturating the region of tissue with fluid without an appreciable bulk flow, including vortex flow. High flow may be applied at 10× or more (e.g., 20×, 50×, 100×, 150×, etc.) the flow rate of the lower flow periods. High flow rate (vortex flow) may be applied oncer per day (e.g., twice pre day, three times per day, four times per day or more, every hour, etc.).

The size adjustment features (e.g., removal channels) may include sizing rings, marking, etc., and can be configured to provide or indicate optional adjustment of the dimensions of a subcutaneous irrigation system. In particular, the removal channels may guide a user, such as a doctor, nurse or medical technician, in removing a predetermined amount and location of material from the apparatus. FIG. 1B shows a detailed view of size adjustment features 107 of the flexible base 105 for a subcutaneous irrigation system as illustrated in FIG. 1A. In this example, there are three size adjustment features 107*a*, 107*b*, and 107*c*, configured as removal channels. Each size adjustment feature that can provide an adjustment for the dimensions of the flexible base 105. While FIG. 1B illustrates an example of a flexible base having three size adjustment channels, the quantity of size adjustment channels may be one or more. In some examples, the flexible base may not have any size adjustment channels.

Figure 1C:
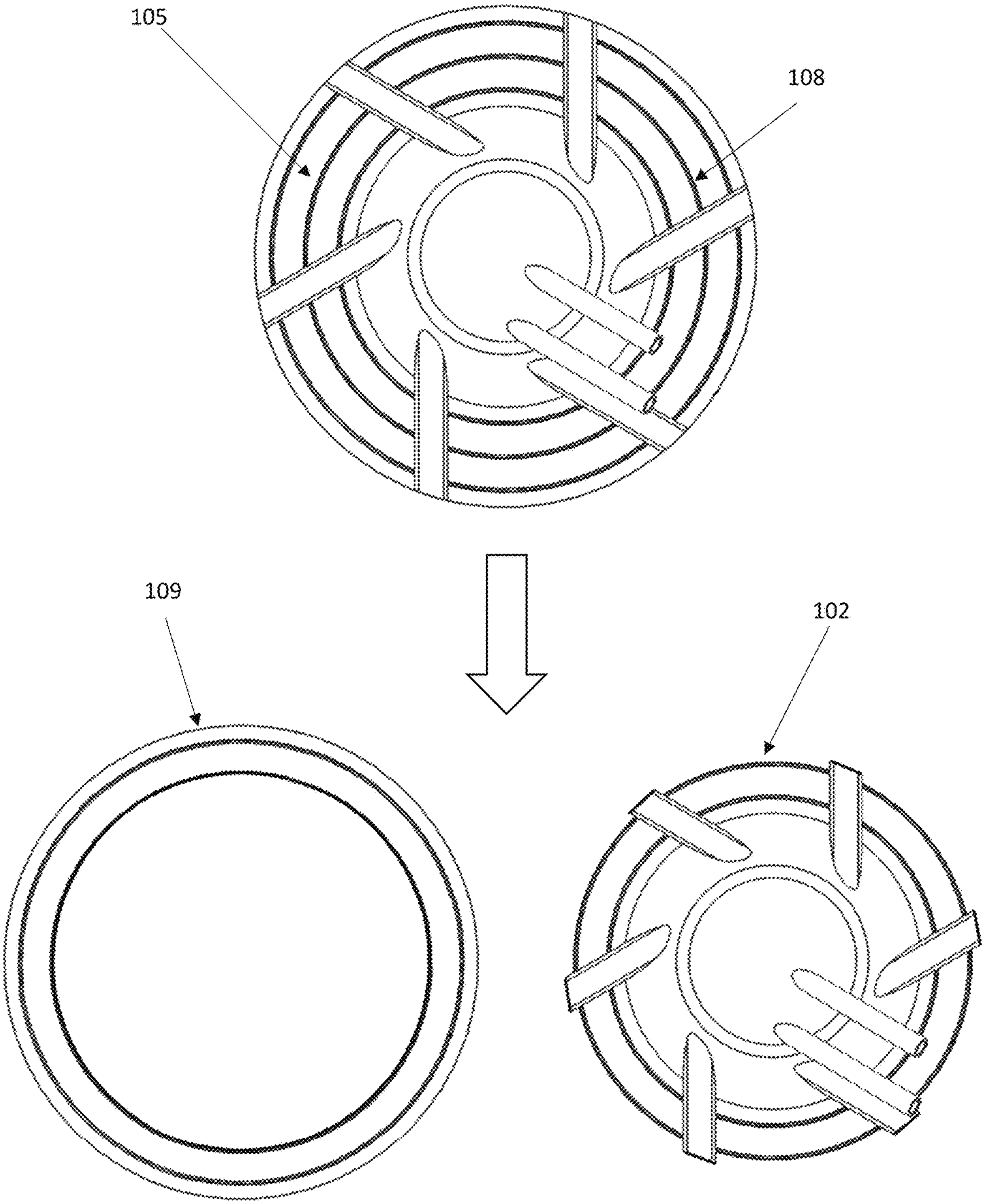
FIG. 1C illustrates removal of a predefined region of the flexible base using a size adjustment channel.

As illustrated in FIGS. 1A, 1B, and 1C, the removal channels 107 in some examples form concentric rings that can be configured to delineate a path whereby the size of the flexible base 105 can be adjusted (e.g., reduced). In some examples, the removal channels 107 may be etched, perforated, thinned, may comprise a different material composition, or other configuration that may provide a different structural integrity in the flexible base material at the along the size adjustment channel to facilitate a change in size of the flexible base 105. For example, to reduce the dimension of the flexible base, a user (e.g., healthcare professional) can pull the distal side 108 of removal channel 107*b* to separate an outer ring (e.g., material distal of removal channel 107*b*) of the flexible base 105, thereby reducing the circumference of the resulting outer perimeter. Referring to FIG. 1C, an example of a transition or change in the size of the flexible base 105 is illustrated whereby the distal side 108 of removal channel 107*b* has been pulled away from the remaining portion of the flexible base resulting in the separated rings 109 and a subcutaneous irrigation system 102.

In some examples, size adjustment channels (e.g., removal channels) may include a visual indication of where a user may cut or trim the flexible base. For example, a removal channels may include a color indicating a certain diameter that a user may select and cut or trim along the sized adjustment element to reduce the dimensions of the subcutaneous irrigation system. In some examples, each removal channels may identify or be identifiable as a predetermined diameter that a user can recognize and adjust or customize the size of the flexible base accordingly. Each removal channels may relate to a predetermined perimeter (e.g., circumference).

Figure 2A:
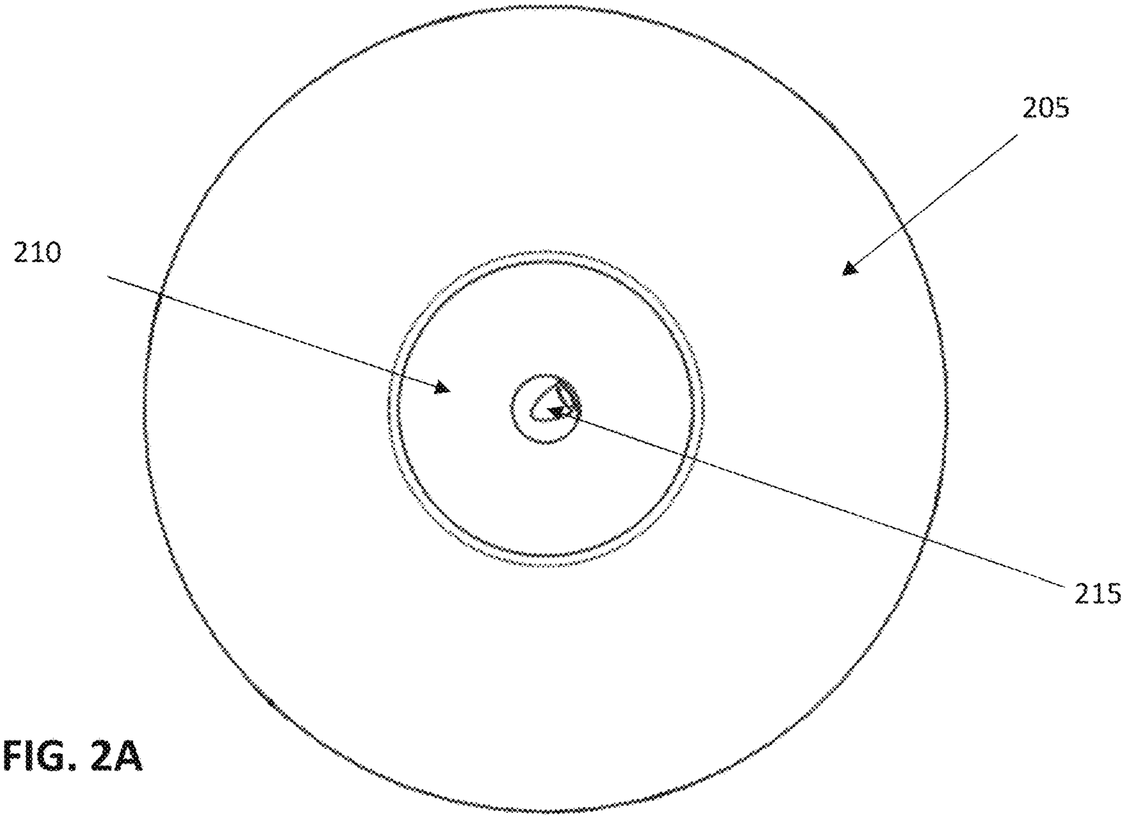
FIGS. 2A and 2B show examples of a subcutaneous irrigation apparatus from a bottom view as described herein.
Figure 2B:
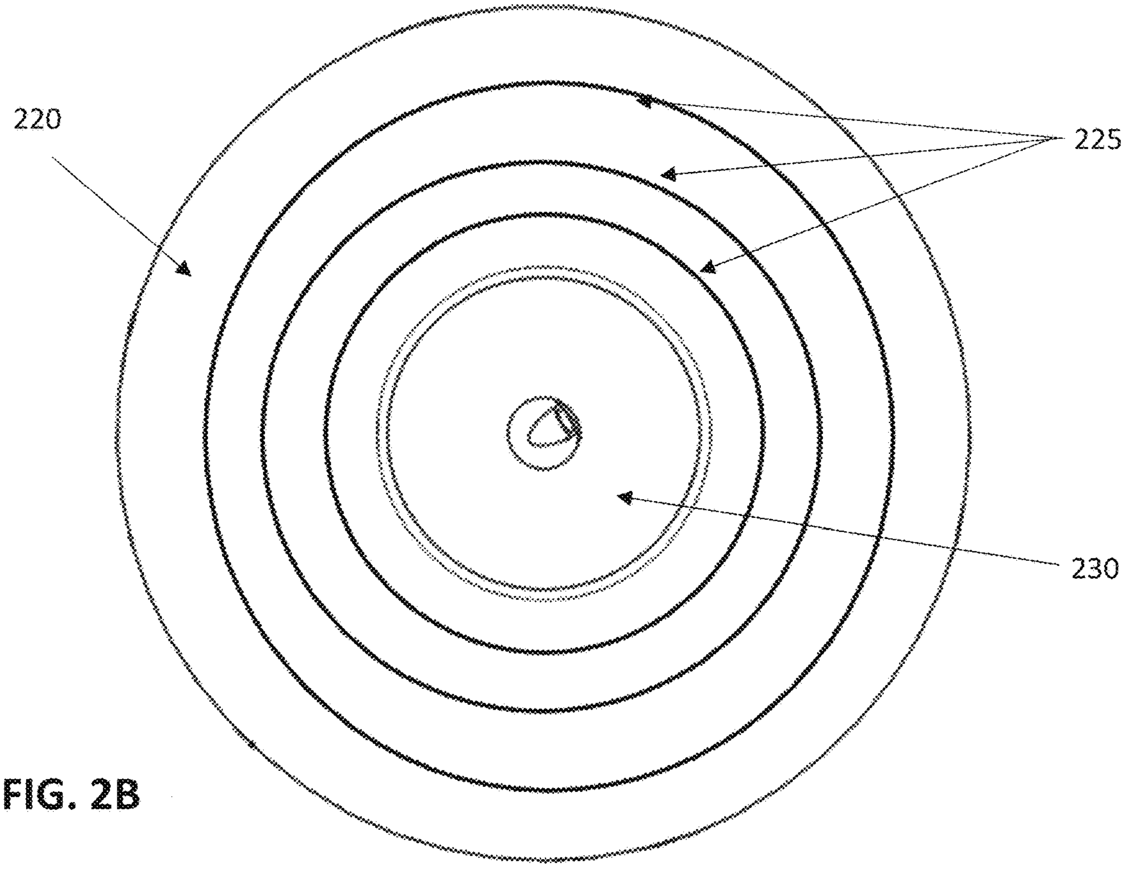

FIGS. 2A and 2B illustrate examples of a subcutaneous system from a bottom side of the flexible base. Referring to FIG. 2A, the flexible base 205 is shown with a hub 210 and a suction port 215. A suction port can be configured to draw fluid (e.g., irrigation fluid). Removal of irrigation fluid may be selectively controlled by the user. For example, suction may be initiated after the flexible base has been placed in the breast pocket before irrigation fluid has been introduced though the irrigation tubes, while irrigation fluid flow from the irrigation tubes, after the irrigation fluids has stopped flowing from the irrigation tubes, or a combination thereof. In some examples, removal of the irrigation fluid may be at a rate relative to the outflow of the irrigation fluid from the irrigation tubes. For example, irrigation fluid may be introduced into a breast pocket at a rate greater than, less than, or equal to the rate fluid is removed via the suction port.

In FIG. 2A, the size adjustment features may not be visible from the bottom surface of the flexible base 205. For example, the size adjustment channels may be visual elements viewed from one side of the flexible base (e.g., a top surface). In FIG. 2B, the bottom surface of the flexible base 220 is shown where the size adjustment channels 225 are visible. The central hub 230 in this example is positioned near the center of the flexible base 220 and the size adjustment channels 225 may be visual indications of predetermined size adjustments or may be etched, perforated, thinned, comprise a different material composition, or other configuration that may provide a different structural integrity in the flexible base material at the along the size adjustment channel to facilitate a change in size of the flexible base 220.

Figure 3:
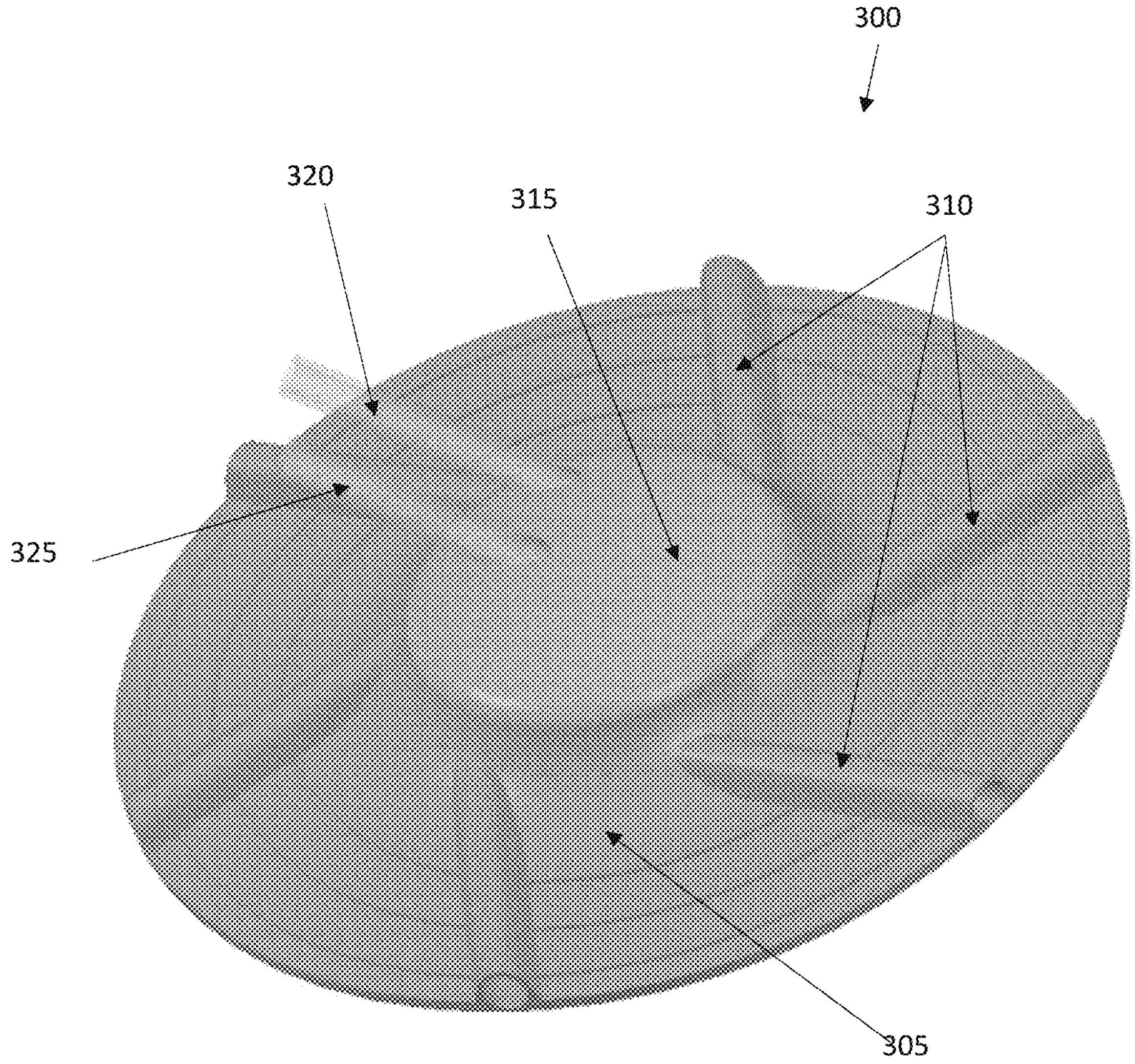
FIG. 3 is a perspective view of an exemplary subcutaneous irrigation apparatus as described herein.

FIG. 3 shows an example of a subcutaneous irrigation system 300 similar to FIG. 1A. Here, details of the irrigation tubes 310 are visible such that the irrigation tubes 310 are integrated into the flexible base 305. In some examples, the irrigation tubes 310 may comprise the same material as the flexible base 305 and may be flexible yet positioned in a static arrangement about the flexible base 305. The angle (e.g., vortex angle, a in FIG. 1B) of each irrigation tube 310 relative to the outer perimeter can provide a flow pattern of irrigation fluid as it leaves the distal opening of an irrigation tube lumen. As shown in FIG. 3, irrigation fluid can flow from the irrigation tubes 310 and form a vortex within the breast pocket. The hub 315 is positioned central in the flexible base 305. Although not visible, the proximal end of each irrigation tube lumen is in operable communication with the central hub 315 to direct fluid flowing therefrom.

In some examples, a central hub can be configured to distribute fluid flowing from a fluid source, through the irrigation tubes. The central hub can also direct the suction or vacuum drawn on the outlet tube to the suction port (not shown in FIG. 3) such that fluids may be removed from the breast pocket to an external container. A central hub may comprise an assembly of one or more pieces (e.g., a top element and bottom element) that may be attached to one another with fluid pathways formed therebetween. In some examples, the hub may comprise a single piece insertable into a flexible base. In some examples, the hub may be replaceable. For example, a base may be insertable into a flexible base such that the hub may be inserted and subsequently removed from the flexible base.

The inlet tube 320 is shown in FIG. 3 in operable communication with the central hub. The inlet tube may be coupled to a fluid source and can direct the fluid from the fluid source to the central hub 315 for distribution through the irrigation tubes 310. The outlet tube 325 is also shown in operable communication with the central hub. The outlet tube 325 may be configured to direct a flow of fluid out from the subcutaneous irrigation system via the suction port. For example, the suction port may be positioned on the opposite side of the central hub 315 and fluid may be drawn from the breast pocket through the suction port, routed through the central hub 315 to the outlet tube 325.

Figure 4:
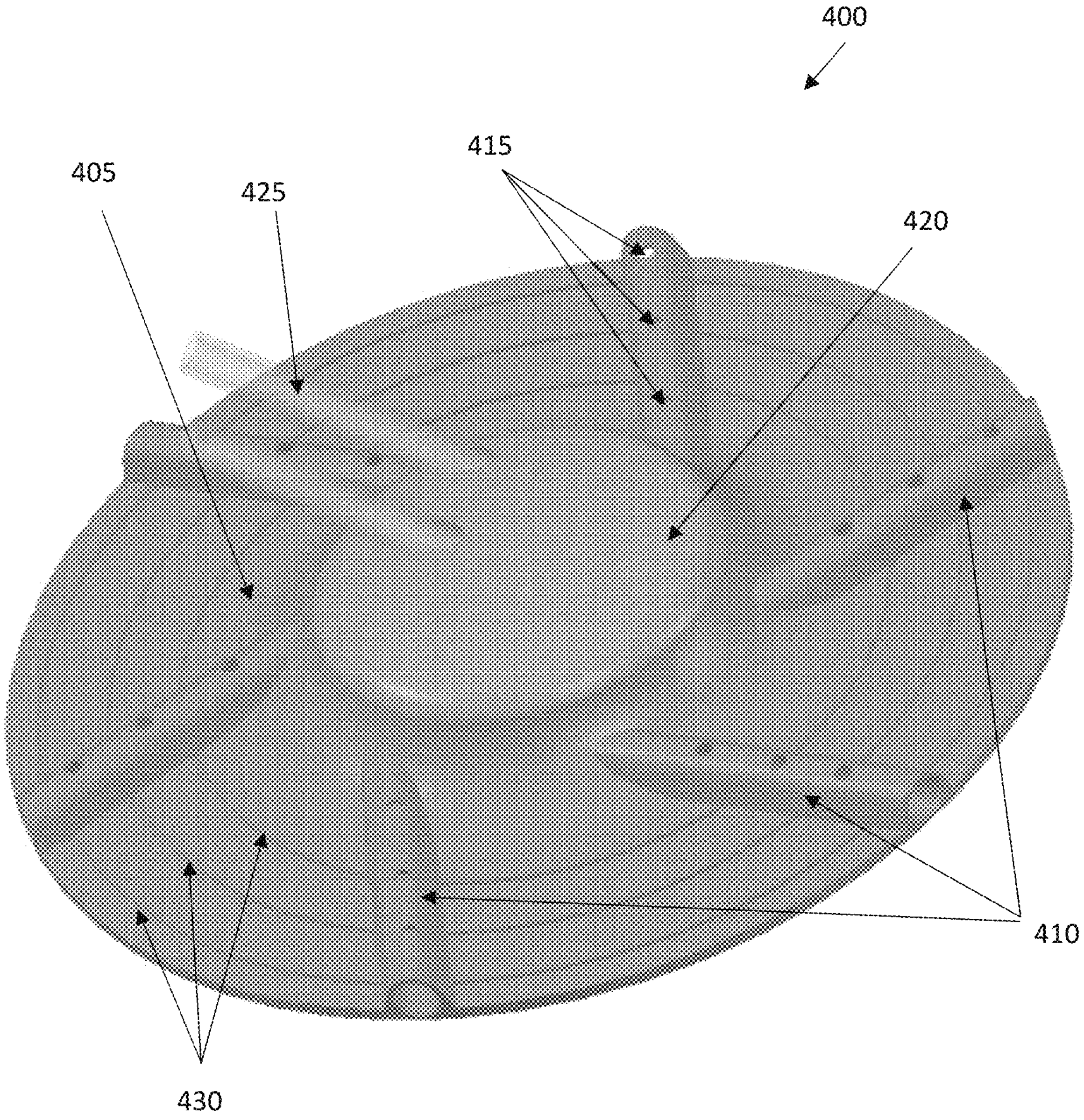
FIG. 4 is a perspective view of an exemplary subcutaneous irrigation apparatus as described herein.

In FIG. 4, a subcutaneous irrigation system 400 is shown having irrigation tubes 410 comprising a plurality of holes 415 positioned along a length of each irrigation tube 410. The holes 415 can be configured to distribute irrigation fluid from the irrigation tubes 410. The flow rate and flow pattern of the irrigation fluid may be influenced by the holes 415. For example, irrigation fluid may flow from the fluid source into the central hub 420 via the inlet tube 425 and be distributed through the irrigation tubes 410 with fluid additionally distributed through holes 415. In some examples, the holes 415 may be configured to adjust a flow or pressure of fluid flowing within and through the irrigation tubes 410. Also shown in FIG. 4 are examples of size adjustment channels 430 each with a reduced diameter and configured to adjust the size of the flexible base 405.

As shown in previous examples, the irrigation tubes 410 extend from the central hub 420 to the perimeter of the flexible base 405. Each irrigation tube 410 extends the entire distance from the central hub to the outer perimeter of the flexible base. One can understand that when the size adjustment channels 430 are removed, the irrigation tube may have a distal end that then extends beyond the adjusted perimeter of the flexible base. For example, when the flexible base size is adjusted by tearing (e.g., removing) one or more of the size adjustment rings, the irrigation tube may remain in its original length (e.g., distance between the central hub and initial perimeter of the flexible base).

In some examples, when a size adjustment channel is removed (e.g., the flexible base is reduced), the size adjustment channel may include a corresponding section of irrigation tube. For example, when the flexible base is adjusted such that the outer ring is removed, the length of irrigation tube from the size adjustment channel to the perimeter may also me removed.

Figure 5:
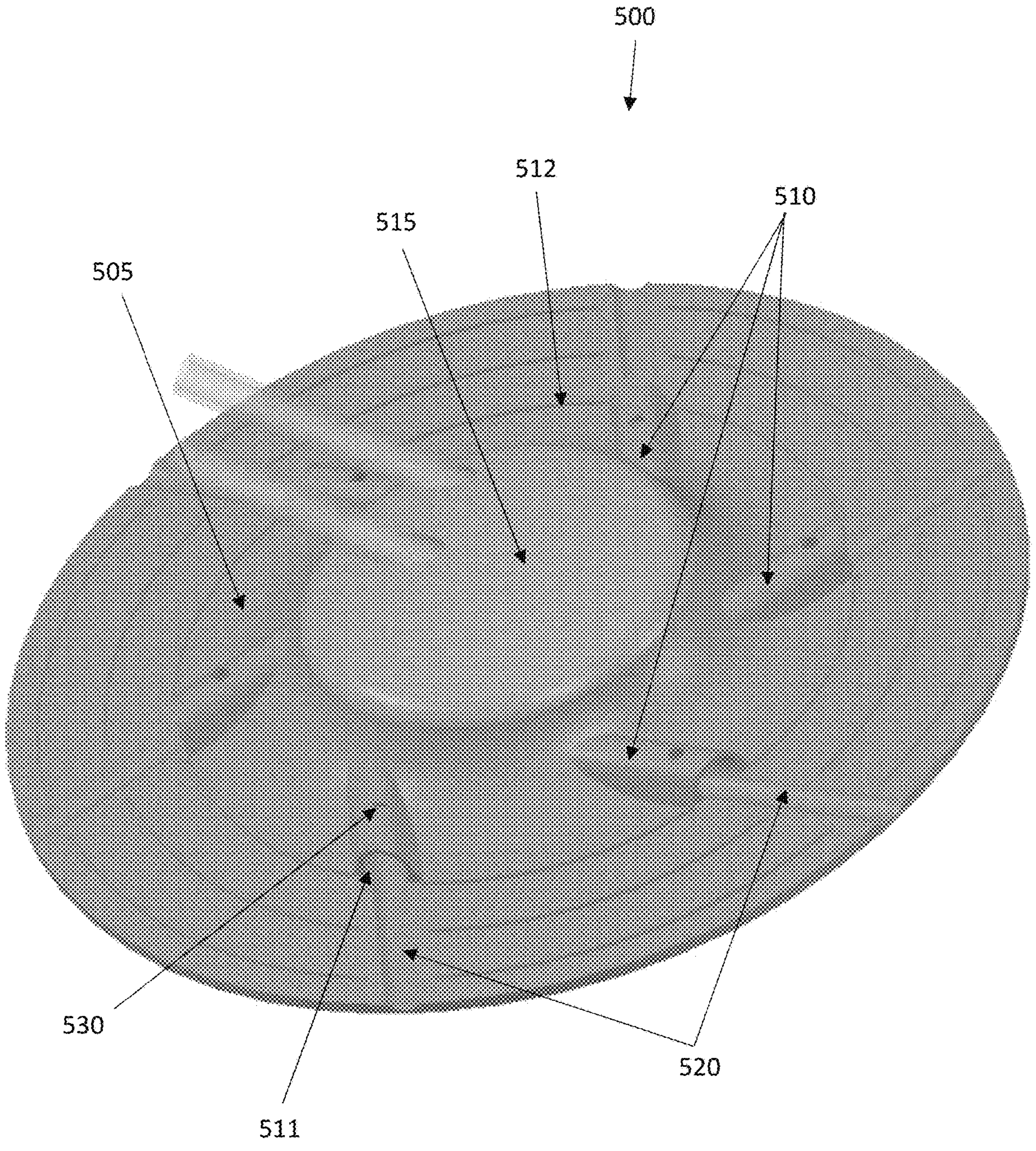
FIG. 5 is a perspective view of an exemplary subcutaneous irrigation apparatus as described herein.

In FIG. 5, a subcutaneous irrigation system 500 is shown having a flexible base 505 with irrigation tubes 510 having a length from the central hub 515 to less than the outer perimeter 506. In this example, the irrigation tubes 510 have a distal opening 511 at or near an inner size adjustment channel 512. Channels 520 are shown to extend from the distal opening 511 of each irrigation tube 510. The channels 520 can provide support in directing a flow of fluid from the distal opening 511 of the irrigation tubes 510 along the surface of the flexible base 505 to an outer perimeter. In this example, the flexible base 505 may be adjusted to a smaller size where the length of a channel would be reduced accordingly. Also shown in FIG. 5, is a configuration with a single hole 530 on each irrigation tube 510. There may be any quantity of holes in any position along a length of each irrigation tube.

Irrigation tubes may have a lumen with a diameter configured to direct and distribute the irrigation fluid into the surgical site (e.g., breast pocket). The diameter of an irrigation tube may impact a flow rate of the irrigation fluid therethrough. Irrigation tubes may also have a length configured to impact the flow rate of irrigation fluid flowing therethrough. The calibration of the flow rate via the length of an irrigation tube, the diameter of the irrigation tube, the number of holes, or a combination thereof can predetermined or adjustable (e.g., via the size adjustment channels. For example, a larger diameter irrigation tube may provide a high flow rate and a smaller diameter irrigation tube may provide a lower flow rate. In some examples, the flow rate may also be influenced by the fluid source. A fluid source may be a bag of irrigation fluid and configured to distribute the irrigation fluid through the subcutaneous irrigation system via gravitational force (e.g., gravity fed). In some examples, the inlet tube may be in communication with a fluid source and a pump configured to pump or distribution irrigation fluid to the subcutaneous irrigation system at a flow rate, pressure, etc. based on the pump.

In some examples, a flexible base may comprise any number of irrigation tubes (e.g., fluid channels). The number of irrigation tubes may adjust a flow rate of irrigation fluid through the system. For example, increasing the number of irrigation tubes may provide a different flow rate. Increasing the number of irrigation tubes may allow for a decreased irrigation tube diameter of each of the irrigation tubes while maintaining the flow rate. As described herein, the angle of the irrigation tubes on the flexible base can provide an angular flow or vortex style flow pattern of the irrigation fluid flowing therefrom. The angular flow may swirl the fluid within the breast pocket and may improve washing and debridement of the surrounding tissue by increasing a Reynolds number and creating more turbulent flow. In some examples, non-angled irrigation tubes (e.g., irrigation tubes extending radially from the hub) may increase a laminar flow of the irrigation fluid.

In some examples, the central hub may comprise a valve configured to adjust flow rates. For example, a central hub may have an adjustment element configured to change a flow rate by adjusting the valve to increase or decrease a volume of fluid distributed through the central hub. The valve may be integrated into the central hub. In some examples, the valve may be adjusted by rotating one or more components of the central hub.

In some examples, the flexible base may be a flexible membrane comprised of silicone, TPU or other flexible material. The flexible base may be sufficiently flexible to allow for insertion through an incision into the breast pocket. The membrane may be colored for visibility or translucent to observe liquid flow through the channels, or a combination thereof.

Figure 6:
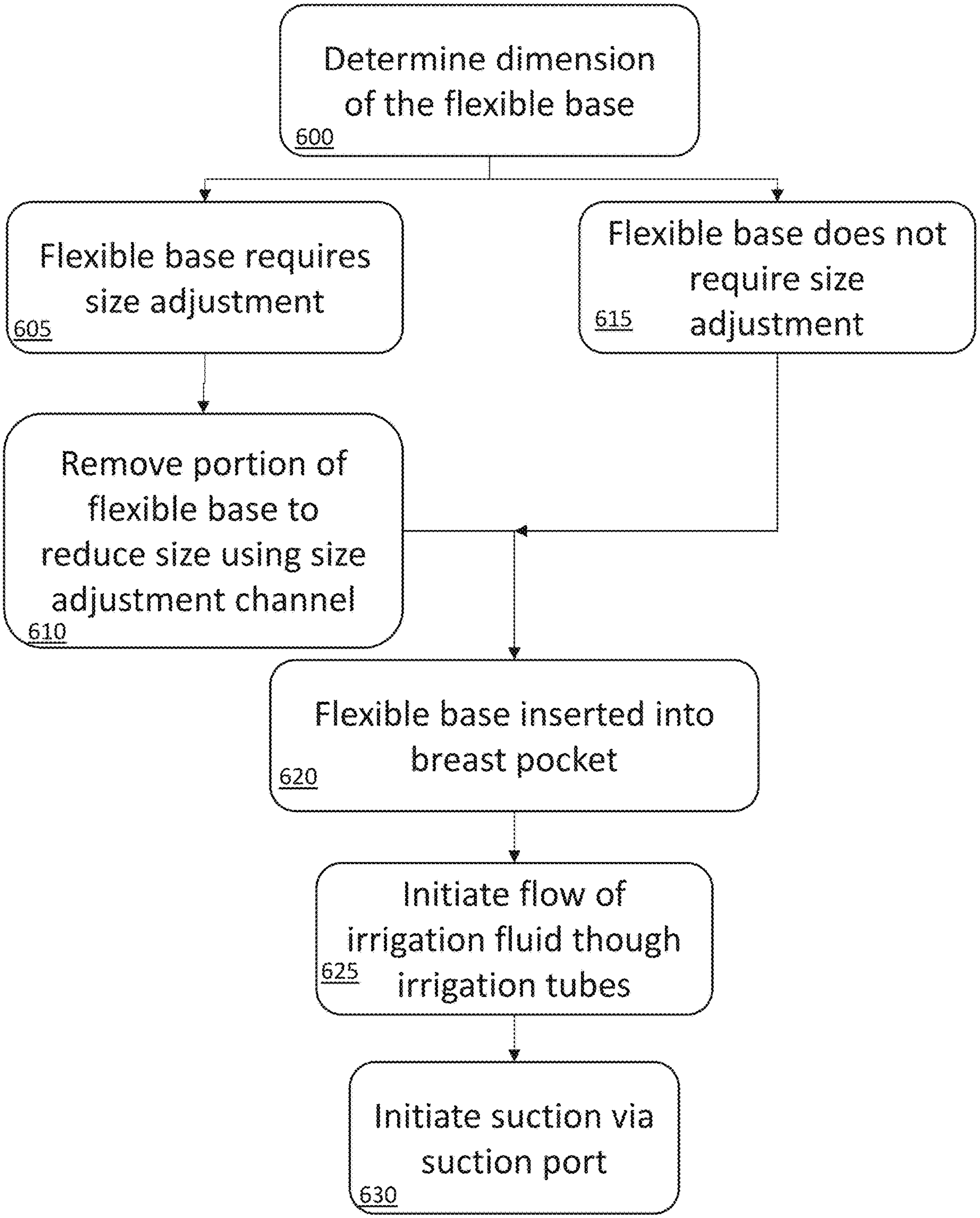
FIG. 6 is a schematic process diagram illustrating an exemplary method of use for a subcutaneous irrigation apparatus as described herein.

FIG. 6 illustrates an example of using a subcutaneous irrigation system described herein. At step 600, the dimensions of the flexible base are determined. The flexible base may have an initial dimension (e.g., circumference) and based on the size of a breast pocket where the system is to be inserted, the size may need to be adjusted. The adjustment, as described herein, may be facilitated by the size adjustment channels. At step 605, the flexible base may require size adjustment. The size adjustment channels may be engaged such that material is removed from the flexible base to reduce the size. At step 610, portions of the flexible base are removed as facilitated by the size adjustment channels. In some examples, at step 615, the flexible base may not need to be adjusted and would not require removal of material via the size adjustment channels. Then, at step 620, the flexible base is inserted into the breast pocket. For example, an incision may be made into the breast and the pocket can be created, then the flexible base can be inserted into the breast pocket via the incision. A flow of irrigation fluid (e.g., triple antibiotic solution, TAS) may be initiated at step 625. The fluid source can be attached to the inlet tube of the irrigation system and fluid flow may be initiated via a valve or switch or gravity when the fluid source is connected. Suction may be initiated at step 630. Although shown subsequent to step 625, suction may be initiated before, during, after, or a combination thereof relative to the flow of irrigation fluid. The suction may be facilitated by the suction port of the central hub and fluid can be directed through the outlet port to an external container.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achie46ve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A subcutaneous irrigation system comprising:

a flexible base comprising a plurality of size adjustment channels configured to remove a predefined amount of the flexible base and a plurality of irrigation lumens; and a hub coupled to the flexible base, the hub comprising an inlet port, an outlet tube, and a suction port, wherein the flexible base is sized and configured to be positioned in a formed subcutaneous pocket, and wherein the plurality of irrigation lumens extend radially away from the hub and are configured to generate a fluid vortex within the formed subcutaneous pocket, wherein each irrigation lumen of the plurality of irrigation lumens is positioned at a vortex angle of between about 10 degrees and about 80 degrees between a midline down the length of the irrigation lumen and a line tangent to a rim of the flexible base from a point where the midline intersects the rim of the flexible base.

2. The subcutaneous irrigation system of claim 1, further comprising one or more holes extending from each irrigation lumen of the plurality of irrigation lumen through the flexible base.

3. The subcutaneous irrigation system of claim 1, wherein the hub is integrated with the flexible base.

4. The subcutaneous irrigation system of claim 1, wherein the hub is configured to distribute fluid through the plurality of irrigation lumens.

5. The subcutaneous irrigation system of claim 1, wherein a perimeter of the flexible base is configured to be reduced by the one or more size adjustment channels.

6. The subcutaneous irrigation system of claim 1, wherein the suction port is positioned on a opposite side of the flexible base from the plurality of irrigation lumens such that the irrigation fluid flows from the irrigation lumens to the suction port.

7. The subcutaneous irrigation system of claim 6, wherein the vortex angle is between about 20 degrees and about 75 degrees.

8. The subcutaneous irrigation system of claim 6, wherein each irrigation lumen of the of the plurality of irrigation lumens extend in straight line.

9. The subcutaneous irrigation system of claim 1, wherein the plurality of irrigation lumens extend radially from the hub.

10. The subcutaneous irrigation system of claim 1, further comprising a flow control valve configured to adjust a flow rate of irrigation fluid.

11. The subcutaneous irrigation system of claim 1, wherein the flexible base is configured to be inserted into a breast pocket.

12. A breast pocket irrigation system comprising:

a flexible base with one or more size adjustment channels configured to reduce a perimeter of the flexible base by a predetermined amount;

a plurality of irrigation tubes coupled to the flexible base, wherein for each irrigation tube of the plurality of irrigation tubes, the irrigation tube is positioned at an angle of between about 10 degrees and about 80 degrees between a midline down the length of the irrigation tube and a line tangent to a rim of the flexible base from a point where the midline intersects the rim of the flexible base;

a central hub comprising an inlet port, outlet tube, and suction port, wherein a proximal end of each irrigation tube is in communication with the central hub.

13. The breast pocket irrigation system of claim 12, wherein the one or more irrigation tubes are angularly positioned around the flexible base and configure to provide a vortex flow of irrigation fluid into the breast pocket.

14. The breast pocket irrigation system of claim 12, wherein each irrigation tube comprises one or more holes extending into a lumen of the irrigation tube.

15. The breast pocket irrigation system of claim 12, wherein the inlet port is configured to couple with an irrigation fluid source.

16. The breast pocket irrigation system of claim 12, wherein the central hub is configured to distribute an irrigation fluid from the inlet port to each of the irrigation tubes.

17. A method of irrigating a breast pocket, the method comprising the steps of:

adjusting a size of a breast pocket irrigation system having a flexible base with size adjustment channels;

inserting the flexible base into the breast pocket;

initiating a flow of irrigation fluid through a central hub of the breast pocket irrigation system, wherein the central hub distributes the irrigation fluid through irrigation tubes coupled to the flexible base, wherein irrigation tube is positioned at an angle of between about 10 degrees and about 80 degrees between a midline down the length of the irrigation tube and a line tangent to a rim of the flexible base from a point where the midline intersects the rim of the flexible base.

18. The method of claim 17, further comprising removing the irrigation fluid from within the breast pocket via a suction port coupled to the central hub.

19. The method of claim 17, wherein the flow of irrigation fluid is distributed by the irrigation tubes in a vortex pattern.

20. The method of claim 17, wherein adjusting the size of the breast pocket irrigation system comprises removing one or more segments of the flexible base via the size adjustment channels.

* * * * *